United States Patent [19]
Willis

[11] Patent Number: 6,023,975
[45] Date of Patent: Feb. 15, 2000

[54] METHOD FOR RAPID DATA ACQUISITION IN RESONANT ULTRASOUND SPECTROSCOPY

[76] Inventor: Frank A. Willis, 442 Sunlight Dr., Powell, Wyo. 82435

[21] Appl. No.: 09/067,316

[22] Filed: Apr. 27, 1998

[51] Int. Cl.[7] .................................................. G01N 29/12
[52] U.S. Cl. .............................................. 73/579; 73/602
[58] Field of Search ........................... 73/579, 602, 593, 73/597, 659, 570, 577, 618, 664; 702/56, 34, 35, 36, 33, 38, 182, 183

[56] References Cited

U.S. PATENT DOCUMENTS

| | | | |
|---|---|---|---|
| 4,111,055 | 9/1978 | Skidmore, III | 73/620 |
| 4,408,285 | 10/1983 | Sisson et al. | 73/602 |
| 4,968,359 | 11/1990 | Hebel, Jr. et al. | 73/579 |
| 5,062,296 | 11/1991 | Migliori | 73/579 |
| 5,355,731 | 10/1994 | Dixon et al. | 73/579 |

*Primary Examiner*—Hezron Williams
*Assistant Examiner*—Helen C. Kwok

[57] ABSTRACT

Data acquisition times from a component under test in resonant ultrasound spectroscopy are decreased. A proximity of each data acquisition point to a resonant response of the component is monitored. A dwell time between successive data acquisition points is then adjusted as a function of the proximity to a resonant response. In one embodiment, each component response is compared to a preselected threshold value and the dwell time between adjacent data points is increased when the response exceeds the threshold value, indicating the response is nearing a resonance. The dwell time is decreased between resonant responses to decrease the data acquisition time.

5 Claims, 2 Drawing Sheets

METHOD FOR RAPID DATA ACQUISITION IN RESONANT ULTRASOUND SPECTROSCOPY

FIELD OF THE INVENTION

This invention relates to non-destructive testing, and, more particularly, to nondestructive testing using resonant ultrasound spectroscopy (RUS).

BACKGROUND OF THE INVENTION

Resonant ultrasound spectroscopy (RUS) is a non-destructive testing method where a manufactured component is subjected to exciting vibrations over a selected frequency spectrum and the resonant responses of the component are detected over the spectrum. Considerable information can be obtained from the distribution of the resonant responses in the spectrum. For example, U.S. Pat. No. 5,062,296, issued Nov. 5, 1991, teaches a method for deriving a characteristic signature of a component, where the signature can be used as an acceptance/rejection criteria. U.S. Pat. No. 5,351,543, issued Oct. 4, 1994, teaches a method for crack detection by comparing RUS spectra in dry and wet conditions. U.S. Pat. No. 5,355,731, issued Oct. 18, 1994, teaches the use of RUS to determine the sphericity of a component.

A significant problem occurs during the data acquisition phase of non-destructive testing using RUS when the driving frequency of the exciting transducer is changed. When a component being tested is vibrated near a natural resonant frequency, the amplitude of the induced vibration decays slowly, i.e., rings, after the driving vibration is removed. If a new exciting vibration frequency is applied while the component is still ringing from a previous exciting frequency, the component requires time to equilibrate to the new frequency. For some period of time there is an interference between the ringing frequency and the applied frequency so that accurate data is not available during that period of time.

Thus, data cannot be collected more rapidly than the ringing permits and the overall speed of the RUS system degrades rapidly near a component resonance. The time period between data collection points is referred to herein as the "dwell" time, or simply "dwell." FIGS. 1A and 1B illustrate the effect of dwell on the collected data. FIG. 1A depicts data taken with a relatively small dwell time (1 ms). The ringing is clearly seen as a succession of oscillations at slightly higher frequencies than the peak frequency. FIG. 1B depicts data taken with a longer dwell time (40 ms) and there is no apparent ringing.

As the amount of dwell is increased, the total time required to collect the necessary data is increased. Consider a set of data such as shown in FIG. 1B. Here, 400 data points were acquired for the single scan. With a dwell of 40 ms for each data point, a total dwell time of 16 seconds (400 points×40 ms/point) is required for the scan. This is time the system is simply waiting for the component to come to equilibrium.

The present invention recognizes that only about 70 of the 400 data points are near the resonance. A long dwell is required only for these 70 data points. Thus, if a dwell of 1 ms is used for all but these points, the total time required to collect the data is reduced to only 3.13 seconds (70 points× 40 ms/point+330 data points×1 ms/point), for a time savings of 12.87 seconds for each scan.

Thus, it is an object of the present invention to minimize the time required for RUS scans of components being tested.

Yet another object of the present invention is to adaptively adjust the dwell for data acquisition.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects, and in accordance with the purposes of the present invention, as embodied and broadly described herein, the method of this invention may comprise a method for reducing data acquisition time from a component under test in resonant ultrasound spectroscopy. A proximity of each data acquisition point to a resonant response of the component is monitored. A dwell time between successive data acquisition points is then adjusted as a function of the proximity to a resonant response to acquire data with relatively short dwell times away from resonance and at long dwell times near resonance.

BRIEF DESCRIPTION OF THE DRAWINGS

The accompanying drawings, which are incorporated in and form a part of the specification, illustrate embodiments of the present invention and, together with the description, serve to explain the principles of the invention. In the drawings.

DETAILED DESCRIPTION

In accordance with the present invention, RUS data acquisition is done with an adaptive dwell time. The amount of dwell required for a component is strongly dependent upon the proximity of the frequency being measured to nearby resonant frequencies. When data is being collected at a frequency far from resonance, only a short dwell time is required. If data is collected near a resonance, a much longer amount of dwell time is required to avoid ringing effects.

In one embodiment of the present invention, an adaptive dwell is implemented for RUS data acquisition. In one implementation, the dwell is a function of the relative amplitude of the output of the response transducer that detects the response of a component to input vibrations. The response of a component will be large in the vicinity of a resonant response and the dwell can be adjusted when the response increases above a selected threshold.

Figure 1A:
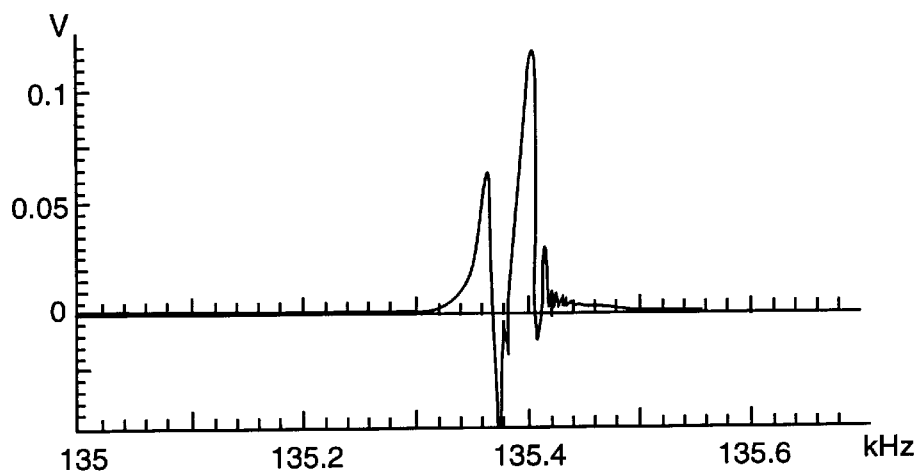
FIG. 1A graphically depicts a resonance scan at a data acquisition dwell time of 1 ms.
Figure 1B:
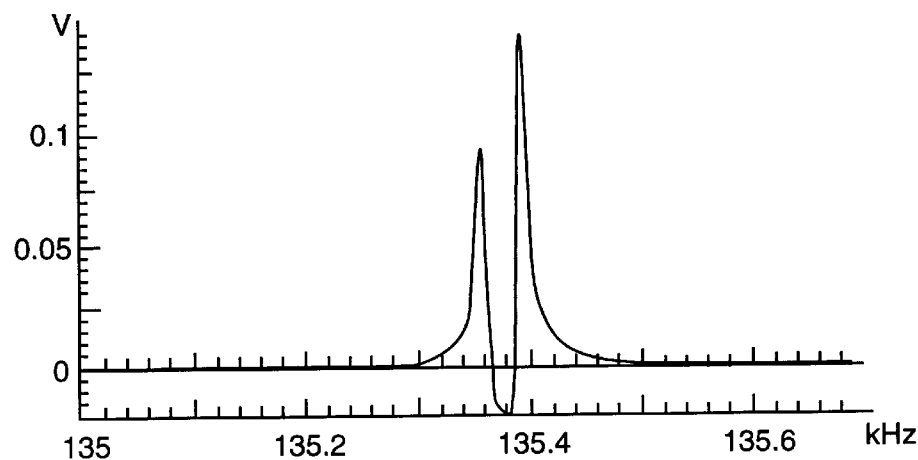
FIG. 1B graphically depicts a resonance scan at a data acquisition dwell time of 40 ms.
Figure 2:
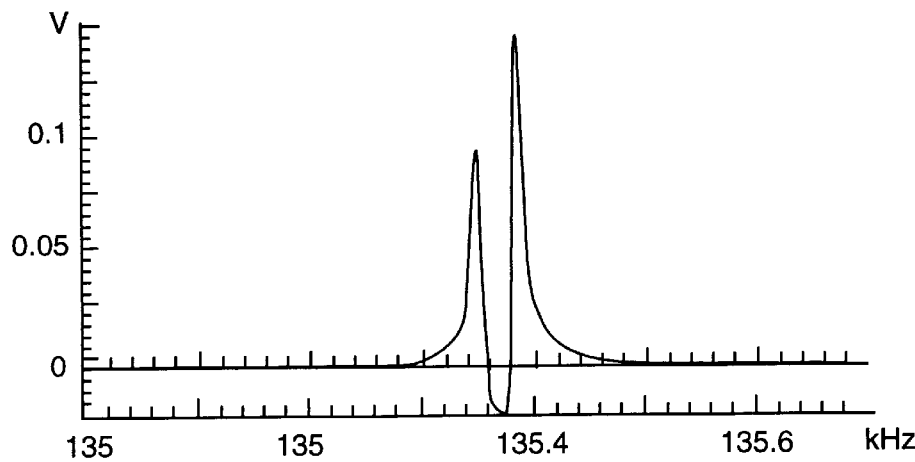
FIG. 2 graphically depicts a resonance scan with an adaptive dwell time in accordance with the present invention.

A threshold can be determined so that one of two dwell times can be selected. If a previous data point has an amplitude less than the threshold value, a relatively short dwell can be used since the point will be sufficiently far from a resonance that ringing is not of concern. If a previous data point has an amplitude greater than the threshold value, then the response is deemed to be approaching a resonance and a relatively longer dwell is selected to permit the component response to equilibrate. FIG. 2 graphically depicts a data scan with a single threshold value, where the dwell is increased from 1 ms to 40 ms when the threshold response value is exceeded. A comparison between FIG. 1B and FIG. 2 shows that there is no ringing in the response, while the data acquisition time was 16 seconds for FIG. 1B and 3.1 seconds for FIG. 2.

A variety of threshold conditions can be selected for adjusting the dwell. In one refinement, a series of thresholds can be used to incrementally increase dwell as resonance is approached.

Figure 3:
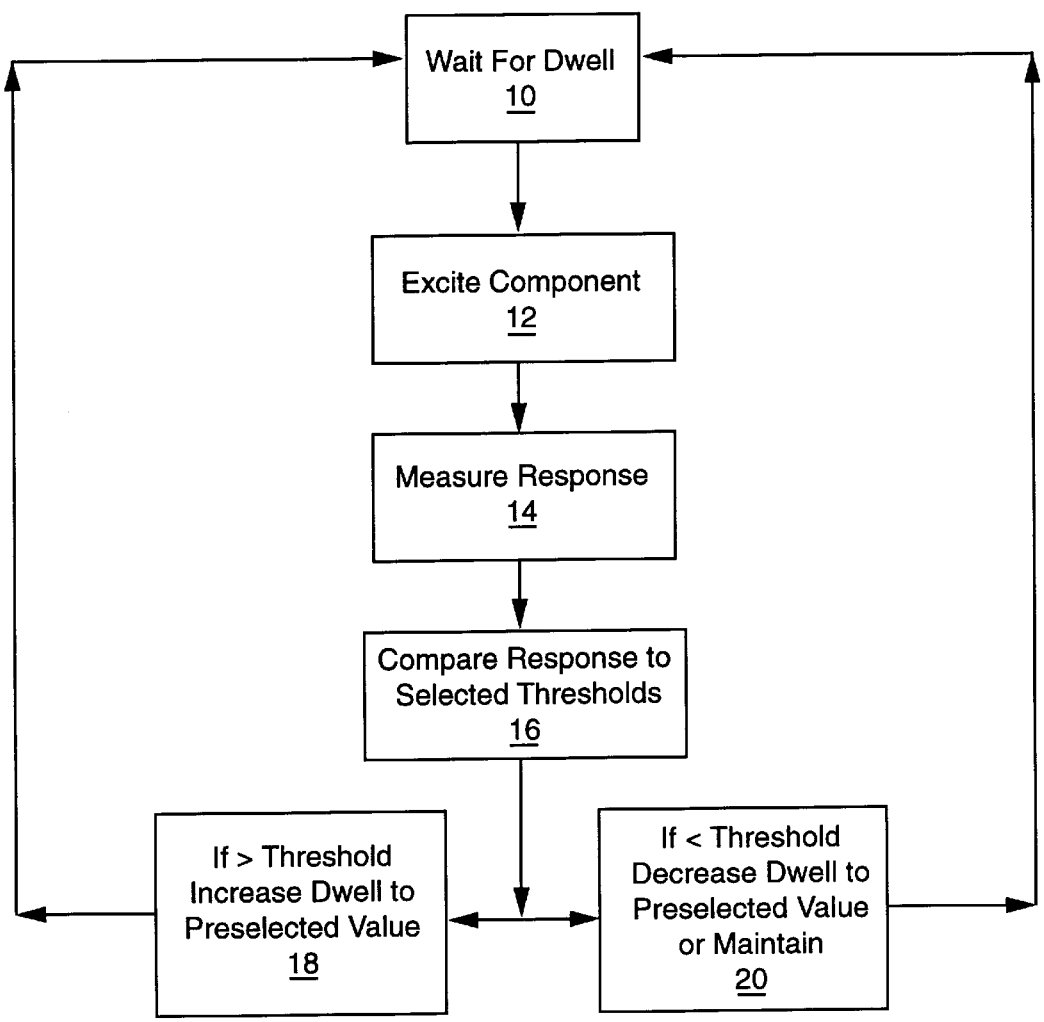
FIG. 3 is a process diagram of the method of the present invention.

FIG. 3 presents a process diagram for implementing the present invention. Data acquisition points for RUS are separated in time by a selected dwell. Once a data point is obtained, the RUS system waits 10 for a selected first dwell time. After dwell, a transducer excites 12 the component under test and the response is measured 14 The response is compared 16 to user selected threshold response values. If the response is greater 18 than the threshold, the dwell is increased to a second selected dwell time that is greater than the first dwell time so that the data dwell is increased as a resonant response is approached. If the response is less 20 than the threshold, the dwell is decreased to a third dwell that is less than or equal to the first dwell time so that the data dwell time is decreased in regions that are not adjacent the resonant response peak. The net effect is to decrease the total data acquisition time for a component while preserving the accuracy of the acquired data.

The foregoing description of the invention for increasing RUS data acquisition has been presented for purposes of illustration and description and is not intended to be exhaustive or to limit the invention to the precise form disclosed, and obviously many modifications and variations are possible in light of the above teaching. The embodiments of the process for adaptively selecting a data acquisition dwell time were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A method for reducing data acquisition time from a component under test in resonant ultrasound spectroscopy, including the steps of:

monitoring a proximity of each data acquisition point to a resonant response of the component; and adjusting a dwell time between successive data acquisition points as a function of the proximity to a resonant response to reduce data acquisition time while maintaining the accuracy of the data acquisition points.

2. A method according to claim 1, wherein the step of monitoring the proximity of each data acquisition point includes the step of comparing each resonant response output to a preselected threshold value.

3. A method according to claim 1, wherein the step of adjusting the dwell time further includes the step of adjusting the dwell time to a relatively long time when approaching a resonant response and to a relatively short time between resonant responses.

4. A method according to claim 3, wherein the step of monitoring the proximity of each data acquisition point includes the step of comparing each resonant response output to a preselected threshold value.

5. A method according to claim 4, wherein the relatively long dwell time is selected when the response exceeds the preselected threshold value and the relatively short time is selected when the response is below the preselected threshold value.

* * * * *